US006475795B1

(12) United States Patent
Turley et al.

(10) Patent No.: US 6,475,795 B1
(45) Date of Patent: *Nov. 5, 2002

(54) USE OF HYALURONAN IN GENE THERAPY

(75) Inventors: Eva A Turley; Samuel S Asculai, both of Toronto (CA)

(73) Assignee: Meditech Research, Ltd., West Perth (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,696

(22) PCT Filed: Oct. 18, 1996

(86) PCT No.: PCT/CA96/00700

§ 371 (c)(1),
(2), (4) Date: Jun. 16, 1997

(87) PCT Pub. No.: WO98/17320

PCT Pub. Date: Apr. 30, 1998

(51) Int. Cl.⁷ ........................ C12N 15/85; C07K 14/00; C07H 22/04

(52) U.S. Cl. ........................ 435/455; 435/455; 530/395; 536/24.5

(58) Field of Search .......................... 514/44; 530/395; 536/24.5

(56) References Cited

U.S. PATENT DOCUMENTS 4,141,973 A    2/1979   Balazs

FOREIGN PATENT DOCUMENTS

| EP | 0 138 572 | 4/1985 |
|----|-----------|--------|
| WO | WO 93/16733 | 9/1993 |
| WO | WO 95/26735 | 10/1995 |
| WO | WO 96/06622 | 3/1996 |
| WO | WO 96/25168 | 8/1996 |
| WO | WO 97/15330 | 5/1997 |

OTHER PUBLICATIONS

Marshall, E. Gene therapy's growing pains. Science vol. 269:1050–1055. Aug. 1995.*
Anderson, W. F. Human gene therapy. Nature vol. 392 (Supp) 25–30. Apr. 1998.*
Verma et al. Gene therapy—promises, problems and prospects. Nature. vol. 389:239–242. Sep. 1997.*
Orkin et al. Report and recomendations of the panel to assess the NIH investment in research on gene therapy. Dec. 1995.*
Aquino et al., *The Journal of Cell Biology*, 99 (3), 1117–1129 (1984).
Bhavanandan et al., *PNAS USA*, 72 (6), 2032–2036 (1975).
Busch et al., *The Journal of Cell Biology*, 116(1), 31–42 (1992).
Citro et al., *PNAS USA*, 89, 7031–7035 (1992).
Constable et al., *Round Table Ser.—R. Soc. Med. Press*, 45 (Fourth International Workshop on Hyaluronan in Drug Delivery), 68–72 (1996).
Da Cruz et al., *Investigative Ophtalmology and Visual Science*, 37 (12), 2447–2454 (1996)
Eggli et al., *Journal of Neurocytology*, 25(2), 79–87 (1996).
Eggli et al., *The Journal of Histochemistry and Cytochemistry*, 43(7), 689–697(1995).
Fedarko et al., *The Journal of Cell Biology*, 102(2), 587–599 (1986).
Ferrari et al., *Haematologica*, 79 (2), 107–111 (1994).
Fraser et al., *Journal of Internal Medicine*, 242, 27–33 (1997).
Fromme et al., *Exp. Cell Res.*, 102, 445–449 (1976).
Furukawa et al., *Biochimica et Biophysica Acta*, 499, 278–789 (1977).
Furukawa et al., *Biochimica et Biophysica Acta*, 585, 575–588 (1979).
Furukawa et al., *Biochimica et Biophysica Acta*, 697, 344–352 (1982).
Gerdin et al., *Journal of Internal Medicine*, 242, 49–55 (1997).
Hiscock et al., *The Journal of Biological Chemistry*, 269(6), 4539–4546 (1994).
Iozzo et al., *The FASEB Journal*, 10, 598–614 (1996).
Ishihara et al., *The Journal of Biological Chemistry*, 261 (29), 13575–13580 (1986).
Kan, *The Anatomical Record*, 228(4), 370–382 (1990).
Liang et al., *The Journal of Cell Biology*, 139(4), 851–861 (1997).
Lindahl et al., *Ann. Rev.Biochem.*, 47, 385–417 (1978).
Margolis et al., *Biochimica et Biophysica Acta*, 451, 465–469 (1976).
Ripellino et al., *The Journal of Cell Biology*, 106, 845–855 (1988).
Ripellino et al., *The Journal of Cell Biology*, 108, 1899–1907 (1989).
Saiga et al., *Experimental Cell Research*, 102 (1), 143–152 (1976).
Sato et al., *Biology of Reproduction*, 37, 371–376 (1987).
Scott, *European Journal of Rheumatology and Inflammation*, 15(1), 3–8 (1995).
Stein et al., *Nature*, 258, 639–641 (1975).
Toole, *Journal of Internal Medicine*, 242, 35–40 (1997).

* cited by examiner

*Primary Examiner*—Terry McKelvey
*Assistant Examiner*—William Sandals
(74) *Attorney, Agent, or Firm*—Leydig, Voit & Mayer, Ltd.

(57) ABSTRACT

A method of treating a human suffering a disease or condition caused by a gene, cDNA or RNA-DNA oligonucleotide or RNA-DNA oligonucleotide hybrids or messenger RNA implicated in a disease or condition involving cells that express hyaluronic acid receptors is provided, the method comprising administering to such human, an effective dosage amount of a pharmaceutical composition comprising an effective amount of a form of hyaluronic acid selected from hyaluronic acid and/or a pharmaceutically acceptable salt thereof associated with/bound with an effective amount of anti-sense to the gene, cDNA or RNA-DNA oligonucleotide or RNA-DNA oligonucleotide hybrids or messenger RNA implicated in the disease or condition in a suitable pharmaceutically acceptable diluent.

8 Claims, 3 Drawing Sheets

FIG. 6
Proliferation of rat hepatoma cells

USE OF HYALURONAN IN GENE THERAPY

BACKGROUND OF THE INVENTION

This invention relates to the use of forms of hyaluronic acid (hyaluronan) in gene therapy. This invention also relates to the use of hyaluronan as a targeting agent in gene therapy to target active agents which ablate the function of targeted genes in the control or treatment of disease and/or conditions.

Hyaluronic acid is a large, complex oligosaccharide consisting of up to 50,000 pairs of the basic disaccharide glucuronic acid-$\beta$(1–3) N-acetylglucos-amine $\beta$(1–4). It is found in vivo as a major component of the extracellular matrix. Its tertiary structure is a random coil of about 50 nm in diameter. Hyaluronic acid appears in nature in its sodium salt form. Hyaluronic acid and its pharmaceutically tolerable or acceptable salts (such as sodium hyaluronate) are identified herein as HA.

HA has the ability to bind a large amount of water, which in vivo makes it a viscous hydrated gel with viscoelastic properties. It is found in this form in the mammalian eye, both in the vitreous and in the extracellular matrix.

HA has been used in the treatment of diseases and conditions of the human body both systemically and topically because of its ability to target an active agent to sites where the disease or condition is located (International Patent Publications No. WO 91/04058 and No. WO 93/16733). It has been shown that HA forms depots for example, at the injured carotid artery (relative to uninjured contralateral arteries) and in colorectal tumours growing in experimental animals, and is retained in the skin of humans and animals. In all these cases, the sites of the deposits are areas of high HA receptor expression, indicating that HA targets specifically to areas for example, of underperfused and pathological tissues that are expressing high levels of these receptors, particularly to tissues undergoing unusual proliferation and migration, including tissues responding to injury, inflammation, development, and tumorigenesis.

Cells of the immune system, including macrophages, neutrophils, T-cells and natural killer cells play a significant role in the conditions described above. These cells rely upon HA receptors to mature into reactive cells that are able to release growth factors and cytokines, as well as oxidizing agents that then set in motion a repair response that contributes to tissue damage. In addition, these cells rely upon HA receptors to adhere to cells such as those of the endothelium and tumour cells and to locomote (migrate) into the site of injury. Tumour cells also require HA receptors to migrate, proliferate and metastasize. Thus, it is possible to interfere with white cell infiltration, for instance into injured rat carotid artery, by adding high concentrations of HA, to inhibit tumour cell proliferation and to block smooth muscle locomotion. Reagents such as function blocking antibodies and peptides mimicking critical regions of the HA receptors are also able to exert the same effect.

Collectively, these results show that HA specifically interacts with unique receptors that occur for example, on the surface of a variety of injured or tumorigenic cells.

Cell surface receptors specific for HA have been identified, including the histocompatibility antigen CD44 and receptor for hyaluronan-mediated motility (RHAMM).

In all of the diseases and conditions discussed above, as well as others, researchers are now attempting to treat the diseases and conditions (for example, restenosis) by gene therapy. The rationale is to ablate a function of a specific gene by either blocking messenger RNA translation to proteins with "antisense" oligonucleotides or gene expression with antisense cDNA. To date, this has largely involved use of these reagents processed within liposomes and by directly applying antisense cDNA's or oligonucleotides to the site of disease. Viruses (for example, adenovirus) have also been proposed but it is difficult to target the viruses to specific sites of disease evidenced by minimal uptake. For example, the process of using viruses which adhere to cells and are taken up by them to target them to DNA is inefficient and the risk of using viruses is to be frowned on and is, for the most part, unacceptable in man. Where gene therapy involves the use of liposomes, it is difficult to target liposomes efficiently and uptake may be even lower than with viruses.

Directly applying the oligonucleotides to the site of injury such as a stenotic plaque has produced beneficial effects in animals but large amounts of oligonucleotides are required and the process prolongs for example, the balloon angioplasty operation which increases the danger to the patient. These results indicate that while gene therapy is a theoretically viable approach to treat disease and conditions, the technical difficulties of efficient targeting and uptake need to be improved.

In an article appearing at page 8 of "The Toronto Star", a daily newspaper published in Toronto, Ontario, Canada on Sep. 22, 1996, there appeared an article discussing the use of gene therapy for the treatment of cancer. The article stated:

"Gene therapy for cancer tries to address the problem of tumors arising because they contain faulty genes. There are several mutant genes that have been implicated in a variety of tumors, but one of the most important is a gene called p53.

In normal cells, p53 helps keep the cell's genetic material in good working order. If there are breaks in the DNA double helix, p53 switches on and initiates DNA repair. If things get out of hand and repair isn't possible, p53 triggers the death of the cell. If such genetic problems go unrepaired, abnormal cell growth—tumors—result.

That is exactly what happens when mutant or nonfunctional versions of p53 arise. The statistics tell the story. At least half of all malignant tumors contain cells with problems in their p53 genes. This includes 80 per cent of colon cancers, 50 per cent of lung cancers, and 40 per cent of breast cancers.

In a small-scale trial reporting in this month's Nature Medicine, a team at the University of Texas treated nine lung cancer patients who had failed all conventional treatment. All had multiple tumors, some of which had metastasized to other organs such as the brain. The gene therapy consisted of injecting good copies of p53 into selected tumor sites.

The technology of delivering genes to tumors is amazing. The genes are placed inside inactivated viruses, tens of millions of viruses per milliliter are injected into the tumor, and some of them invade cancer cells and presumably integrate their genetic package—including the "good" p53—into those cells.

In the Texas trial, two of the patients either couldn't complete the trial or died before its completion. In three of the remaining seven, the tumor treated with gene therapy actually shrank. In three others, the tumor, while not shrinking, showed no signs of growth. One patient showed complete regression of the tumor. Programmed cell death inside the tumor, a process known to be initiated by active p53 genes, was seen in six of the patients.

Remember, these were patients for whom conventional cancer therapy held no hope. In fact, many of them died within months of the trial from the growth of other tumors that had not been targeted by the gene therapy."

The suppression of expression of genes encoding proteins which mediate undesirable activity has been achieved in a variety of situations by the introduction of 'anti-sense' DNA sequences into the DNA of target cells. These anti-sense sequences are DNA sequences which, when transcribed, result in synthesis of RNA whose sequence is antiparallel to the sequence encoding the protein. Such anti-sense sequences have been tested in a number of viral diseases. Alternatively, anti-sense oligodeoxynucleotides can be introduced into target cells; such short sequences are not themselves transcribed, but inhibit transcription and/or subsequent translation of the corresponding sense DNA sequence in the target cell.

Until recently it was widely thought that the minimum sequence length necessary in order to effect anti-sense inhibition of gene expression was 12 to 14 nucleotides (Wagner, 1994). However, it has now been shown that the specificity of binding to the target sequence can be sufficiently enhanced by the use of modified oligonucleotides comprising C-5 propyne pyrimidines and phosphorothioate internucleotide linkages that sequences as short as 7 or 8 nucleotides are effective in providing gene-selective, mismatched sensitive, ribonuclease H-dependent inhibition, in which flanking sequences of the target RNA are important in determining specificity (Wagner, et al, 1996).

However, successful use of anti-sense nucleotides to counter expression of a gene in vivo is limited by factors such as the need for co-suppression of mutant gene expression (Milan, 1993; McInnes and Bascom, 1992), or the need for high concentrations of the anti-sense nucleotides (Akhtar and Ivinson, 1993).

To date, this form of therapy has largely involved use of anti-sense sequences packaged in liposomes, or direct application of antisense cDNA or oligonucleotides to the site of disease (review 14.14a). Thus, attempts to increase uptake of anti-sense sequences into the target cell by encapsulating these sequences in liposomes have been largely unsuccessful. It is also difficult to target liposomes efficiently, and uptake is even lower than with viruses. Directly applying the oligonucleotides to a site of injury such as a stenotic plaque has produced beneficial effects in animals, but large doses of oligonucleotides are required, and the process prolongs the balloon angioplasty operation, thus increasing the danger to the patient.

Targeting of the gene therapy has also been tried using viruses for example, an adenovirus to achieve virus-mediated DNA transfer.

Adenoviruses have been widely used for gene transfer in both non-dividing and proliferating cells. They can accommodate DNA up to 7.5 kb, and provide efficient transfection and high viral titre. The main disadvantages of adenoviruses is their transient gene expression and the risk of their use. This is a result of the lack of integration of the transgene into the cellular genome. Thus, this process is inefficient, and the use of viruses may entail, and usually does, an undesirable level of risk of iatrogenic disease.

It is therefore an object of this invention to provide improved methods of targeting gene therapy in a human for the treatment of disease and conditions, the manufacture of suitable compositions comprising a form of hyaluronan for the use in such treatment, improved uses of the product/composition comprising a form of hyaluronan targeting gene therapy and pharmaceutical compositions comprising forms of hyaluronan suitable for use in gene therapy.

Further, and other objects of the invention, will be appreciated by those skilled in the art from the following summary of the invention and detailed description of embodiments thereof.

SUMMARY OF THE INVENTION

Whatever gene therapy is to be used for the treatment of a disease or condition involving the treatment of cells expressing receptors for hyaluronan, the treatment by gene therapy is enhanced by combining the therapy with an effective amount of a form of hyaluronan (hyaluronic acid) such as sodium hyaluronate, such as preferably in an amount of at least about 50 mg of the form of hyaluronan per 70 kg person such as about 500 mg of the form of hyaluronan per 70kg person (for example, where the gene therapy involves the treatment of cells expressing receptors for forms of hyaluronan). The effective amount of the gene therapy agent may now be an effective amount less than the usual or accepted amount understood to be used alone by persons skilled in the art to be used in the treatment because of the enhanced delivery by the form of hyaluronan to the nucleus of the cells. These amounts of the form of hyaluronan are calculated based on the results of the tests herein (use in the tests of 100 $\mu$g/ml of the form of hyaluronan and lesser amounts such as 10$\mu$g/ml—see page 22 of this document) and the fact that there is about 5 liters of blood in an average human (70 kg. person). The total amount of water in a human of average weight (70 kg) is approximately 40 liters, (i.e. 0.55 L/kg), averaging 57% of his/her total body weight. About 25 liters of the 40 liters of fluid in the body are inside the approximately 75,000,000,000,000 cells of the body and are collectively called the "intracellular fluid ".

The extracellular fluid (the remaining fluid) can be divided into interstitial fluid, plasma, cerebral spinal fluid, intra-ocular fluid, and fluids of the gastro-intestinal tract. The total amount of fluid in the extracellular compartment averages about 15 L/70 kg adult, (i.e. 0.2 L/kg).

Blood contains both extracellular fluid (the fluid of the plasma) and intracellular fluid (the fluid in the red blood cells). The average blood volume of a normal adult is almost exactly 5 liters. On the average, approximately 3 liters of this is plasma and the remainder, 2 liters, is red blood cells.

Persons skilled in the art will appreciate that variations in the weight of patients will alter the effective amounts of the form of hyaluronic acid used in each treatment of the patient taking gene therapy. The adjustment is expected to be proportional to the weight of the person being treated. A person weighing for example, 100 kg will preferably be given at least about 71.4 mg for example, about 714 mg of the form of hyaluronic acid. Such lower amount of the form of hyaluronic acid per person may be reduced slightly and still be effective (for example, to 49 or 48 mg/70 kg person). The greater the reduction, the less will be the effectiveness. However, if the for example, 500 mg amount of the form of hyaluronic acid is increased in the patient's treatment, such amount may be 1000 mg or more. As there is no toxicity of hyaluronic acid, the form of hyaluronic acid may be used in larger amounts without adverse effects. Such amount may exceed 1500 mg or more, such as 3000 mg.

Therefore, according to one aspect of the invention a form of hyaluronan (for example, hyaluronic acid and/or pharmaceutically acceptable salts thereof such as sodium hyaluronate) is bound to (for example, non-covalently bound to)/associated with anti-sense to (of) a gene, cDNA or RNA-DNA oligonucleotide or RNA-DNA oligonucleotide hybrids or messenger RNA implicated in a disease or condition and the product is administered to a patient in an effective amount in a suitable diluent and by any suitable route of administration such as intravenous administration, injection, etc. to ablate the function of the targeted gene or genes in the control or treatment of the disease and/or condition for example, where the cells being treated and thus, the nucleii whose genetic make-up is being modified, express HA receptors such as RHAMM and CD-44 for example. Such treatment is administered for such period necessary to treat the disease or condition. A suitable amount of the form of hyaluronan for each treatment comprises in excess of about 50 mg/70 kg person preferably about 500 mg/70 kg person and is adjusted up or down by the weight of the patient to whom the composition is administered. The suitable amount of HA with the gene therapy is given for such time as is necessary for treating the disease or condition such as for such time needed to resolve the disease or condition. The amount of the gene therapy agent may be reduced from that normally used in ordinary gene therapy treatment without a form of hyaluronan because of the enhanced transport by the form of hyaluronan.

Possible methods for binding/attaching the hyaluronan to the antisense (DNA) are many and are exemplified in two articles discussed below:

Synthesis of Sulfonated Hyaluronan Derivatives containing Nucleic Acid Bases, Wada, T., Chirachanchai, S., Izawa, N. Takemoto, K. Chemistry Letters 1994 (11), 2027–2030 (1994);

and,

Transport performance of nucleotides through nucleic acid bases conjugated hyaluronan, Chirachanchai, S., Wada, T., Inaki, Y. Takemoto, K.: Chemistry Letters, 1995(2): 121–122 (1995 Article Feb abstract on computer)

We have now shown in this Application that interaction of HA (labeled with a fluorochrome) to the cell receptors results in uptake of HA into the cytoplasm and nucleus of the cells. This process is rapid, occurring within minutes and culminates in the accumulation of the receptor/hyaluronan complex within and around the nucleus wherein genetic material is located. Thus, hyaluronan associated with/bound to gene therapy (such as DNA anti-sense), interacts with cell receptors resulting in the uptake of the HA and the gene therapy into the cell and into the nucleus.

According to another aspect of the invention, the anti-sense cDNA or oligonucleotide or oligonucleotide hybrid to a gene which is to be treated (neutralized) in a human, may be combined (such as bound) with the form of hyaluronic acid (hyaluronan) and then the combination administered to the patient intravenously unlike the prior art proposals, which involve the use of viruses, liposomes or direct application of oligonucleotides which each have a low efficiency of uptake or which are not target specific or which are not recommended for human use (such as viruses).

Thus, according to another aspect of the invention, this invention relates to the manufacture of anti-sense cDNA or oligonucleotide or oligonucleotide hybrid to the gene or messenger RNA related to (implicated in) the disease or condition to be treated wherein the anti-sense cDNA or oligonucleotide or oligonucleotide hybrid is associated with/ bound to a form of hyaluronan (as described above) and the combination is administered to the patient such as to neutralize the gene. As hyaluronic acid is taken up by the receptors which are expressed at high levels in the areas of the disease or condition for example, injury, inflammation, the anti-sense cDNA or oligonucleotide or oligonucleotide hybrids is brought into or near the nucleus by receptor endocytosis cDNA or oligonucleotides or oligonucleotides hybrids which then permits the anti-sense to neutralize the relevant gene and thus, prevents in either case the protein for example, produced by the gene, from being produced.

Thus, according to another aspect of the invention, new compositions are provided comprising the product of a form of hyaluronan and anti-sense to a gene implicated in diseases or conditions of the human body bound/associated together with a suitable diluent (such as sterile water).

One form of gene therapy is the use of RNA-DNA oligonucleotide. In this therapy treatment, the correcting of a mutated form of an extrachromosomal gene (such as in sickle cell anemia) or the plasmid is accomplished by use of a chimetic oligonucleotide composed of DNA and RNA residues. For example, a short, double-stranded vector is activated for recombination by incorporating RNA residues and protected from exonucleolytic degradation by capping both ends. The 2'OO-methyl modification of ribose of the RNA added protection against cleavage by ribonuclease (RNase) H activities.

To correct the $\beta^s$ mutation (for sickle cell anemia, for example), the chimeric oligonucleotide (SCl) was designed as a single molecule (with two sequences that were inverted and complementary) capable of folding back on itself to form a duplex structure. The molecule was composed of DNA residues with two intervening blocks of 10 2'-O-methyl RNA residues flanking a short stretch of five DNA residues. When the molecule was folded into the duplex conformation, the sequence of one strand comprised all DNA residues whereas the other strand contained the RNA-DNA blocks. In this case, the internal sequence is complementary to the $\beta^s$- globin sequence over a stretch of 25 residues that span the site of the $\beta$mutation, with the exception of a single base (T). The five DNA residues flanked by RNA residues were centered about the mutant T residue in the $\beta^s$ coding sequence. A control chimeric oligonucleotide (SC2) was designed in the same manner with the exception of one base.

This chimeric molecule was previously introduced (see "Correction of the Mutation Responsible for Sickle Cell Anemia by an RNA-DNA Oligonucleotide", Cole-Strauss, Allyson et al., Science, Vol. 273, Sep. 6, 1996, pp. 1386–8) into the lymphoblastoid cells ($\beta$cells) homozygous for the $\beta^s$ allele by means of a commercial liposome formulation.

The chimeric molecule can now be introduced by means of an effective amount of a form of hyaluronan. Thus, according to another aspect of this invention, this chimeric molecule may now be introduced to the human to be treated accompanied by a form of hyaluronic acid taking the chimeric molecule into each cell to accumulate within and around the nucleus wherein genetic material is located which genetic material within the cell is then mediated.

An effective amount of the form of hyaluronan administered is in excess of about 50 mg/70 kg person, for example in excess of 500 mg/70 kg person for example, by intravenous administration in a suitable excipient (e.g. sterile water) for such time as is necessary.

Thus, according to various aspects of the invention, there is provided:

a) a composition comprising a form of hyaluronan associated with/bound to anti-sense nucleic acid;

b) a method of treatment comprising the step of administration of anti-sense nucleic acid associated with/ bound to a form of hyaluronic acid; and c) the use of a form of hyaluronan (such as hyaluronic acid and pharmaceutically acceptable salts thereof {e.g. such as sodium hyaluronate}) and anti-sense nucleic acid in the manufacture of a pharmaceutical composition comprising a combination of the form of hyaluronan and anti-sense nucleic acid such as an anti-sense nucleic acid-hyaluronic acid complex together with a suitable diluent for the treatment of a human suffering from a disease or condition treatable using gene therapy.

Many forms of hyaluronan may be suitable for use herein although those preferred are those discussed hereinafter. Particularly, molecular weights of forms of hyaluronan between about 150,000 daltons and about 750,000 daltons in sterile water prepared having a viscosity for intravenous administration are suitable.

One specific form of pharmaceutical grade is a 1% sterile sodium hyaluronate solution (50 ml vials) provided by Hyal Pharmaceutical Corporation which has the following characteristics:

| Tests | Specifications |
| --- | --- |
| 1. Container Description | 1 50 mL Flint glass vial with a red or gray rubber stopper and an aluminum seal, 20 mm in size. |
| 2. Product Description | A clear, colourless, odourless, transparent, slightly viscous liquid. |
| 3. Fill Volume | 50.0 to 52.0 mL |
| 4. pH | 5.0 to 7.0 at 25 degrees C. |
| 5. Specific Gravity | 0.990 to 1.010 at 25 degrees C. |
| 6. Intrinsic Viscosity | 4.5 to 11.0 dL/g |
| 7. Molecular Weight | 178,000 to 562,000 daltons |
| 8. Sodium Hyaluronate Assay and Identification | 9.0 to 11.0 mg/mL. Positive |
| 9. Particulate Matter | No visible Particulate Matter |
| 10. Sterility | Meets Requirements for Sterility, USP 23 |
| 11. Bacterial Endotoxins (LAL) | Meets Requirements for Bacterial Endotoxins, USP 23. |

This pharmaceutical grade 1% sterile solution of hyaluronan may be made from granules/powder having the following characteristics:

| Tests | Specifications |
| --- | --- |
| 1. Description | White or cream-coloured granules or powder, odourless |
| 2. Identification (IR Spectrum) | Must conform with the Reference Standard Spectrum. |
| 3. pH (1% Solution) | Between 5.0 and 7.0 at 25 degrees C. |
| 4. Loss on Drying | NMT 10.0% at 102 degrees C. for 6 hours. |
| 5. Residue on Ignition | Between 15.0 and 19.0% |
| 6. Protein Content | NMT 0.10% |
| 7. Heavy Metals | NMT 20 ppm (as per USP 23 p. 1727). |
| 8. Arsenic | NMT 2 ppm (as per USP 23, p. 1724). |
| 9. Residual Solvents | a) Acetone: NMT 0.1% b) Ethanol: NMT 2.0% c) Formaldehyde: NMT 100 ppm |
| 10. Sodium Hyaluronate Assay | 97.0 to 102.0% (dried basis) |
| 11. Intrinsic Viscosity | Between 10.0 to 14.5 deciliters per gram. |
| 12. Molecular Weight (calculated using the Laurent Formula) | Between 500,000 to 800,000 daltons (based on intrincis viscosity). |
| 13. Total Aerobic Microbial Count | NMT 50 microorganism/gram (as per USP 23, p. 1684). |
| 14. Test for *Escherichia coli* | *Escherichia coli* is absent (as per USP 23, p. 1685). |
| 15. Yeasts & Molds | NMT 50 microorganisms/gram (as per USP 23, p. 1686). |
| 16. Endotoxins (LAL) | NMT 0.07 EU/mg (as per USP 23, p. 1696). |

A topical grade of hyaluronan may, in certain circumstances be suitable and may be made from the following granules/powder which have the following characteristics:

| Tests | Specifications |
| --- | --- |
| 1. Description | White or cream-coloured granules or powder, odourless |
| 2. Identification (IR Spectrum) | Must conform to the Reference Standard Spectrum. |
| 3. pH (1% Solution) | Between 6.0 and 8.0 at 25 degrees C. |
| 4. Loss on Drying | NMT 10.0% at 102 degrees C. for 6 hours. |
| 5. Residue on Ignition | Between 15.0 and 19.0% |
| 6. Protein Content | NMT 0.40% |
| 7. Heavy Metals | NMT 20 ppm (as per USP 23 p. 1727). |
| 8. Arsenic | NMT 2 ppm (as per USP 23, p. 1724). |
| 9. Residual Solvents | a) Acetone: NMT 0.1% b) Ethanol: NMT 2.0% c) Formaldehyde: NMT 100 ppm |
| 10. Sodium Hyaluronate Assay | 97.0 to 102.0% (dried basis) |
| 11. Intrinsic Viscosity | Between 11.5 to 14.5 deciliters per gram. |
| 12. Molecular Weight (calculated using the Laurent Formula) | Between 600,000 to 800,000 daltons (based on intrinsic viscosity). |
| 13. Total Aerobic Microbial Count | NMT 100 microorganism/gram (as per USP 23, p. 1684). |
| 14. Test for *Staphylococcus aureus* | *Staphylococcus aureus* is absent (as per USP 23, p. 1684). |
| 15. Test for *Pseudomonas aeruginosa* | *Pseudomonas aeruginosa* is absent (as per USP 23, p. 1684). |
| 16. Yeasts & Molds | NMT 200 CFU/gram (as per USP 23, p. 1686). |

This topical grade may then be sterilized.

Other forms may be suitable such as one form of hyaluronic acid and/or salts thereof (for example, sodium salt) may be an amount also supplied by Hyal Pharmaceutical Corporation. One such amount is a 15 ml vial of Sodium hyaluronate 20 mg/ml (300 mg/vial—Lot 2F3). The sodium hyaluronate fraction is a 2% solution with a mean average molecular weight of about 225,000. The amount also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with contents of the vial.

The amount of hyaluronic acid and/or salts thereof (for example sodium salt) may comprise hyaluronic acid and/or salts thereof having the following characteristics:

a purified, substantially pyrogen-free-fraction of hyaluronic acid obtained from a natural source having at least one characteristic selected from the group consisting of the following:
  i) a molecular weight within the range of 150,000–225,000;
  ii) less than about 1.25% sulphated mucopolysaccharides on a total weight basis;

iii) less than about 0.6% protein on a total weight basis;
iv) less than about 150 ppm iron on a total weight basis;
v) less than about 15 ppm lead on a total weight basis;
vi) less than 0.0025% glucosamine;
vii) less than 0.025% glucuronic acid;
viii) less than 0.025% N-acetylglucosamine;
ix) less than 0.0025% amino acids;
x) a UV extinction coefficient at 257 nm of less than about 0.275;
xi) a UV extinction coefficient at 280 nm of less than about 0.25; and,
xii) a pH within the range of 7.3–7.9. Preferably, the hyaluronic acid is mixed with water and the fraction of hyaluronic acid fraction has a mean average molecular weight within the range of 150,000–225,000.

Preferably this amount of hyaluronic acid comprises at least one characteristic selected from the group consisting of the following characteristics:
i) less than about 1% sulphated mucopolysaccharides on a total weight basis;
ii) less than about 0.4% protein on a total weight basis;
iii) less than about 100 ppm iron on a total weight basis;
iv) less than about 10 ppm lead on a total weight basis;
v) less than 0.00166% glucosamine;
vi) less than 0.0166% glucuronic acid;
vii) less than 0.016% N-acetylglucosamine;
viii) less than 0.00166% amino acids;
ix) a UV extinction coefficient at 257 nm of less than about 0.23;
x) a UV extinction coefficient at 280 nm of less than 0.19; and
xi) a pH within the range of 7.5–7.7

Other forms of hyaluronic acid and/or its salts may be chosen from other suppliers, for example those described in prior art documents disclosing forms of hyaluronic acid having lower molecular weights between about 150,000 daltons and 750,000 daltons being prepared as for example, 1–2% solutions in sterile water for intravenous administration. In addition, sodium hyaluronate produced and supplied by LifeCore™ Biomedical, Inc. having the following specifications may be suitable (if sterile):

| Characteristics | Specification |
|---|---|
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive Response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |
| As  Cd  Cr  Co  Cu  Fe  Pb  Hg  Ni | |
| 2.0  5.0  5.0  10.0  10.0  25.0  10.0  10.0  5.0 | |
| Microbial Bioburden | None observed |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture Where high molecular weight hyaluronic acid (or salts or other forms thereof) is used, it must, prior to use, for example with the anti-sense, be diluted to permit administration and ensure no intramuscular coagulation. Recently, it has been found that large molecular weight hyaluronic acid having a molecular weight exceeding about 1,000,000 daltons self-aggregates and thus, does not interact very well with HA receptors. Thus, the larger molecular weight hyaluronic acid should be avoided (such as Healon™).

U.S. Pat. 4,141,973 teaches hyaluronic acid fractions (including sodium salts) having:
(a) an average molecular weight greater than about 750,000, preferably greater than about 1,200,000—that is, a limiting viscosity number greater than about 1400 $cm^3/g$., and preferably greater than about 2000 $cm^3/g$.;
(b) a protein content of less than 0.5% by weight;
(c) ultraviolet light absorbance of a 1% solution of sodium hyaluronate of less than 3.0 at 257 nanometers wavelength and less than 2.0 at 280 nanometers wavelength;
(d) a kinematic viscosity of a 1% solution of sodium hyaluronate in physiological buffer greater than about 1000 centistokes, preferably greater than 10,000 centistokes;
(e) a molar optical rotation of a 0.1–0.2% sodium hyaluronate solution in physiological buffer of less than $-11 \times 10^3$ degree—$cm^2$/mole (of disaccharide) measured at 220 nanometers;
(f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being
(g) sterile and pyrogen free and
(h) non-antigenic.

Thus, according to an aspect of the invention, the invention provides a composition comprising gene therapy agent bound to/associated with hyaluronic acid or a derivative thereof, together with a pharmaceutically-acceptable diluent.

As indicated, the gene therapy agent may be a nucleotide sequence which is in the anti-sense orientation to a target sequence. The target sequence is a nucleic acid sequence which is implicated in the causation or exacerbation of a pathological condition. This target nucleic acid sequence may be a gene, genomic DNA, a cDNA, a messenger RNA or an RNA-DNA oligonucleotide or RNA-DNA oligonucleotide hybrid. Where the target nucleic acid sequence is a genomic DNA, it may be present in a coding region preferably incorporating RNA residues capping both ends for protection from exonucleolytic degradation or in a regulatory region.

Alternatively, the gene therapy may comprise a nucleic acid sequence to be transferred into a target cell. The nucleic acid sequence may be genomic DNA, cDNA, messenger RNA, or an RNA-DNA oligonucleotide or an RNA-DNA oligonucleotide hybrid. In this case, the nucleic acid may either be a sense sequence to be provided to a target cell in order to exert a function, or may be an anti-sense sequence to be provided to inhibit the functioning of a nucleic acid present in the target cell.

The invention also provides a method of treatment of a pathological condition in a subject in need of such treatment, comprising the step of administering an effective dose of a composition according to the invention to said subject over a period as may be required. One dose may, in some cases, be effective while in other cases, the treatment may continue for months.

It will be clearly understood that the dose and route of administration will depend upon the condition to be treated, and the attending physician or veterinarian will readily be able to determine suitable doses and routes. It is contemplated that the compositions of the invention may be administered by intravenous administration, injection, topically for example, adsorbed on gels or sponges, or directly into the tissue to be treated for example, by intra-ocular or intra-tumoral injection.

The subject to be treated may be a human, or may be an animal.

The invention further provides a method of preparing a composition of the invention, comprising the step of combining such as binding a gene therapy agent, as discussed above, with hyaluronan and/or a pharmaceutically-acceptable salt thereof, and isolating the thus-formed associate and combining same with a diluent (such as sterile water) and put into a suitable pharmaceutically acceptable tolerable form (which is of course, non-toxic).

BRIEF DESCRIPTION OF THE FIGURES

Thus, FIG. 1 (identified as A) is a photograph of hyaluronan labelled with CY-3 fluorochrome added to the living cells at time, t=0 showing intracellular uptake of the HA.

FIG. 2 (identified as Figure B) is a photograph of the combination at time, t=5 minutes after addition.

FIG. 3 (identified as Figure C) is a photograph of the combination at time, t=10 minutes after addition.

FIG. 4 (identified as Figure D) is a photograph of the combination at time, t=20 minutes after addition.

From reviewing the photographs in FIGS. 1 to 4 (photographs A, B, C, and D), it is clear that as shown in photograph C (FIG. 3), the hyaluronan labelled with CY-3 fluorochrome has penetrated into the cytoplasm into the nucleus and surrounds the nucleus (the dark circle centrally located in Figure C now surrounded by light-coloured hyaluronan labelled fluorochrome after 10 minutes after the introduction of the hyaluronan labelled fluorochrome).

Figure 1:
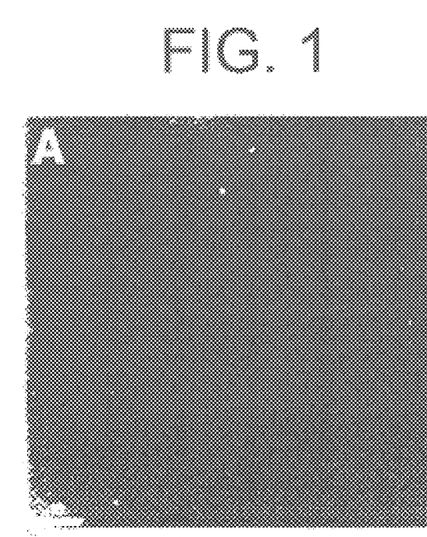
FIGS. 1–4 (Figures identified as photographs A, B, C, and D) illustrate the in vitro uptake of hyaluronan (HA) at various times to the cells and nucleus wherein hyaluronan has been labelled with CY-3 fluorochrome covalently linked to the hyaluronan and added to line cells (Fibroblasts).
Figure 2:
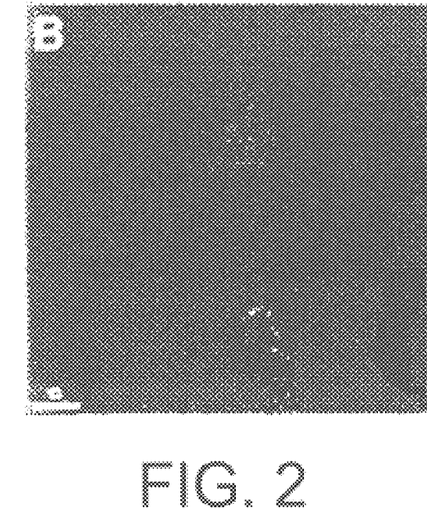
Figure 3:
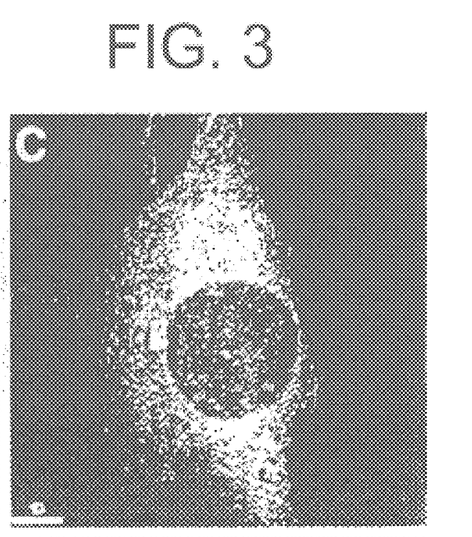
Figure 4:
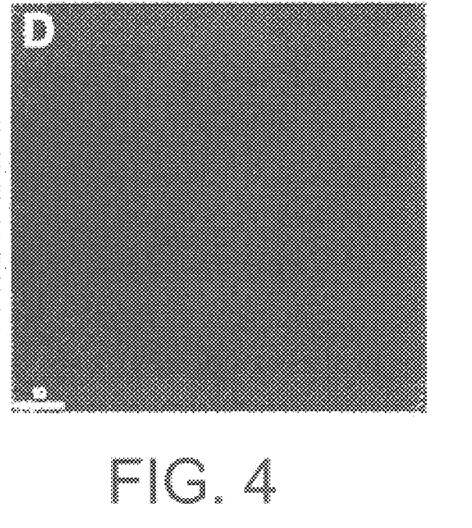

After 20 minutes, the hyaluronan has disappeared, perhaps having been pumped out from the cell or degraded. The cells have been photographed using a confocal microscope using lasers that slice through the cell layer so that the cytoplasma HA (hyaluronan) can be seen.

Figure 5:
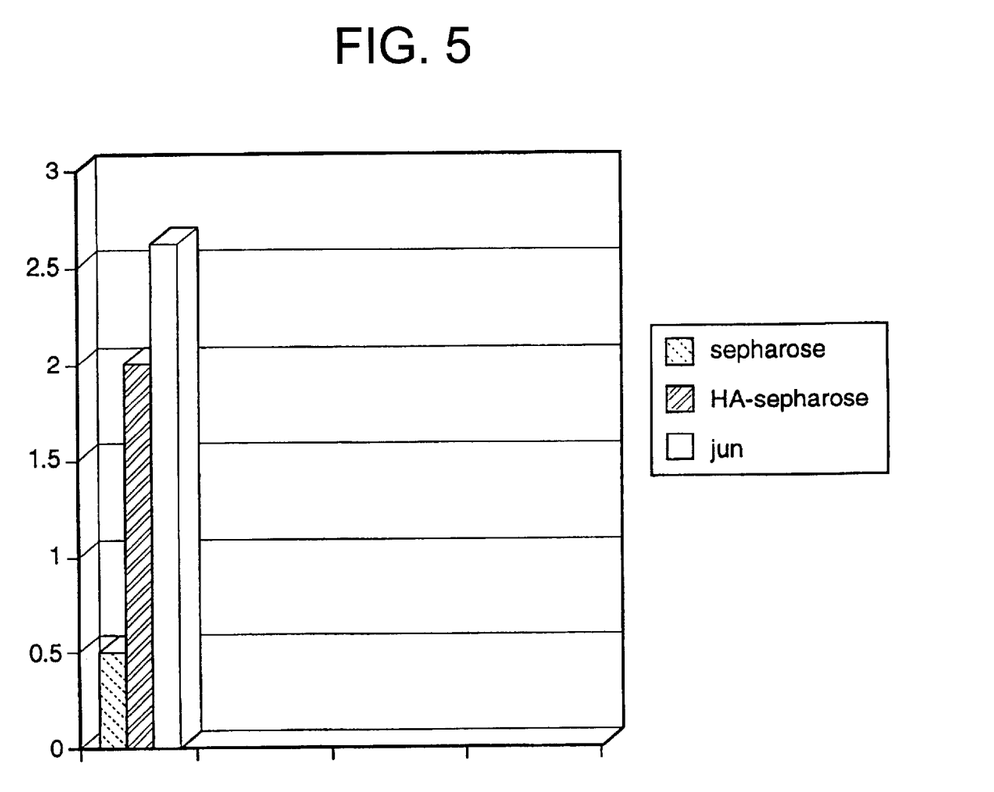
FIG. 5 is a graphical representation illustrating that hyaluronan binds to DNA.

With reference to FIG. 5, hyaluronan-SEPHAROSE, SEPHAROSE alone and the transcription factor, jun-SEPHAROSE (a positive control) were incubated with genomic DNA. Bound DNA was amplified with polymerase chain reaction (PCR) and DNA was run on an agarose gel. The gel was photographed and the optical density determined. From the results shown in the graphical representation, it is clear that HA binds DNA.

DETAILED DESCRIPTION OF EMBODIMENTS OF THE INVENTION

The invention will now be described by way of reference only to the following non-limiting examples.

The following tests were conducted. The purpose was to target antisense RNA/DNA to tumor cells and to enhance uptake of these oligonucleotides reducing the concentration required for biological efficacy. To this end, the method utilizes the hyaluronan polysaccharide to efficiently enhance uptake of nucleotides into the cell and target these to the nucleus and other intracellular compartments (see FIGS. 1–4, photographs A, B, C, and D).

The hyaluronan binds to RNA/DNA when mixed and interacts with high affinity with the HA receptors RHAMM and CD44[12]. Interaction of HA with these receptors causes the rapid internalization of HA and its targeting to the nucleus and other parts of the cell (see FIG. 3—photograph "C"). This rapid uptake enhances the availability of antisense oligonucleotides for inhibition of RNA translation or DNA transcription.

Results

A rat 1548 hepatoma cell line was chosen from the lines that express differing levels of RHAMM and CD44 (see Table A,B). The rat line 1548 expressed the highest levels of RHAMM and CD44 relative to primary hepatocytes and other hepatocyte cell lines.

Figure 6:
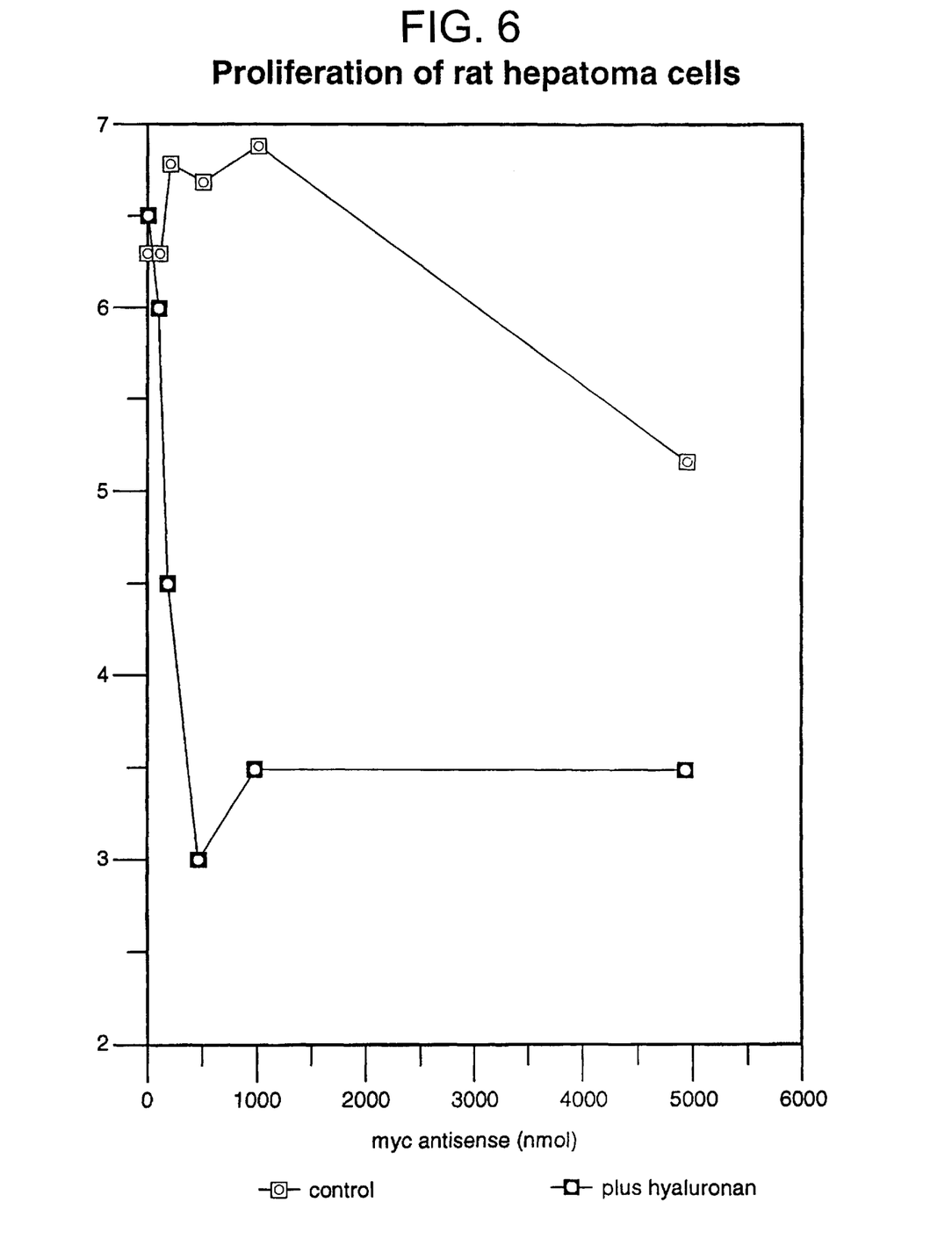
FIG. 6 is a graphic representation entitled "Proliferation of rat hepatoma cells".

As shown in FIG. 6, myc antisense oligonucleotides inhibited proliferation of the 1548 cell line by 17% at 5,000 nmol of myc antisense oligonucleotide. The addition of 100 $\mu$g/ml of HA reduced this requirement for oligonucleotide to 500 nmol and at this concentration further enhanced inhibition of proliferation to 53%. (In other tests, lesser amounts such as about 10 $\mu$g/ml of HA were used successfully). When the concentration of oligonucleotide was further reduced to 200 nm in the presence of the 100 $\mu$g/ml of HA, inhibition was 32%. The results were much less dramatic for cell lines that did not express high levels of RHAMM or CD44.

To assess whether the effects of HA were due to an interaction specific to the myc antisense oligonucleotide, an antisense oligonucleotide was designed to disrupt RHAMM synthesis. This HA receptor regulates the MAP kinase cascade that controls proliferation and progress through G1 of the cell cycle. When this antisense oligonucleotide was used, a 42% inhibition of proliferation was obtained with 1000 nmol RHAMM antisense alone while a 37% inhibition was obtained with 50–100 nmol antisense oligonucleotide in the presence of HA.

These results indicate that HA reduces the concentration requirement (and thus, the amount) for antisense oligonucleotides by for example, 20–25 fold in cells expressing HA receptors (100 $\mu$g/ml of HA). This effect was noted for both RHAMM and myc antisense oligonucleotides indicating that the effect is a general one. We conclude that HA is an effective targeting agent to cells (both cytoplasm and nucleus) that express HA receptors [1,2]. HA receptors have been shown to be upregulated during tumorgenesis, embryogenesis and inflammatory processes.[1.]

References:

1. Sherman, K., Sleeman, J., Herrlich, P. and Ponta, H. 1994 Curr. Opin. Cell Biol. 6,726–733

2. Entwistle, J., Hall, U. and Turley, E. A. 1996 J. Cell. Biochem. 61:569–577
3. Hall, L. L., Yang, B., Yang, X., Zhang, S., Turley, M., Samuel, S., Lange, C. A, Wang, C., Lupen, G. D., Savani, R. C., Greenberg, A. A. and Turley, E. A. 1995 Cell. 82:19–28

TABLE A

RHAMM (V4)

| Cell Line | Expression | Location | | |
|---|---|---|---|---|
| | | Membrane | Cytoplasma | Nucleus |
| 1548 | (++) | (±) | (+) | (+++) |
| 1602 | (+) | (±) | (+) | (++) |

TABLE B

CD44 (SD)

| Cell Line | Expression | Location | | |
|---|---|---|---|---|
| | | Membrane | Cytoplasma | Nucleus |
| 1548 | (++) | (++) | (++) | (+) |
| 1602 | (++) | (±) | (+) | (++) |

The use of HA in this invention transports the gene therapy agent to the cells which express HA receptors into the cell and thus, into the cytoplasm and into the nucleus. This is because effective amounts of the forms of HA will bind cell membranes and other molecules simultaneously and penetrate into the nucleus taking the effective amount of gene therapy into the cells. If sufficient HA is given to be effective for the human to receive effective amounts of the gene therapy agent for effective treatment of all cells (which may be an amount reduced from the usual amounts tried and given by persons skilled in the art because of the effectiveness of the forms of HA), then the treatment can be effective. However, sufficient amounts of each are to be given. The ability of the HA molecule to bind with/carry the RNA-DNA oligonucleotide, for example and the cell membrane at the same time, therefore, increases the contact time of the gene therapy around the cell and the nucleus.

As many changes can be made to the amounts of HA and gene therapy without departing from the scope of the invention disclosed herein, it is intended that all material contained herein be illustrative of the invention and not in a limiting sense.

The embodiments of the invention in which an exclusive property or privilege is claimed are as follows:

1. A method of enhancing uptake of a nucleic acid by a cell comprising contacting said cell with a composition comprising a nucleic acid associated with or bound to hyaluronic acid or a salt thereof.

2. The method of claim 1 wherein the hyaluronic acid or salt thereof has a molecular weight less than 750,000 daltons but greater than about 150,000 daltons.

3. The method of claim 1 wherein the composition is sterile.

4. The method of claim 1, wherein said composition further comprises an excipient.

5. The method of claim 1 wherein the hyaluronic acid or salt thereof has a molecular weight less than 750,000 daltons.

6. The method of claim 5 wherein the hyaluronic acid has a molecular weight greater than about 150,000 daltons.

7. The method of claim 1, wherein the cell expresses hyaluronic acid receptors and wherein the hyaluronic acid or salt thereof binds to the cell and effects targeted delivery of the nucleic acid.

8. The method of claim 7, wherein the cell is a cancer cell.

* * * * *